United States Patent [19]

Mikura et al.

[11] 4,167,563

[45] Sep. 11, 1979

[54] TRH SOLUTION

[75] Inventors: Yasushi Mikura, Senriyamahigashi; Yoshiharu Matukura, Izumoihonmachi; Hiroshi Fujisawa, Uenohigashi, all of Japan

[73] Assignee: Takeda Chemical Industries, Ltd., Osaka, Japan

[21] Appl. No.: 835,815

[22] Filed: Sep. 22, 1977

[30] Foreign Application Priority Data

Oct. 1, 1976 [JP] Japan .................................. 51-118875

[51] Int. Cl.$^2$ ............................................. A61K 37/02
[52] U.S. Cl. ............................ 424/177; 260/112.5 TR
[58] Field of Search ............... 424/177; 260/112.5 TR

[56] References Cited

U.S. PATENT DOCUMENTS 4,059,692  11/1977  Takahashi et al. ................... 424/177

FOREIGN PATENT DOCUMENTS 980238  1/1965  United Kingdom .

*Primary Examiner*—V. D. Turner
*Attorney, Agent, or Firm*—Wenderoth, Lind & Ponack

[57] ABSTRACT

An injectable solution containing a trihydric to hexahydric sugar alcohol together with L-pyroglutamyl-L-histidyl-L-prolinamide or a physiologically acceptable salt thereof shows significantly reduced pain when administered to a host, especially subcutaneously or intramuscularly.

9 Claims, No Drawings

TRH SOLUTION

The present invention relates to an injectable solution containing L-pyroglutamyl-L-histidyl-L-prolinamide (thyrotropin-releasing hormone; hereinafter referred to as TRH) or a physiologically acceptable salt thereof.

Injectable solutions of TRH or its salts are generally used as a diagnostic reagent for testing the thyrotropin-secreting function of the pituitary gland, and are also of value as drugs for the management of impaired consciousness due to functional or organic damage of the brain (refer to German Patent Application Laid-Open (OLS) No. 26 11 976).

However, the known injectable solution which is prepared merely by dissolving TRH in physiological saline, when administered subcutaneously or intramuscularly, produces an intense pain even if it contains TRH only at a low concentration of the order of 0.1 mg./ml. The intensity of this pain is not substantially altered even if the hydrogen ion concentration of the solution is varied with its osmotic pressure being kept isotonic with sodium chloride, that is to say, even if the pH of the solution is varied within the range of 3 to 7.5 with hydrochloric acid, sodium hydroxide or the like, which phenomenon indicates that the pain is emanated from the inherent characteristics of TRH. The research undertaken by the present inventors to develop an injectable TRH solution, rendered painless with a substance which is physiologically completely harmless and which does not decrease the shelf-life of the solution, led to a finding that the concomitant presence of a trihydric to hexahydric sugar alcohol along with TRH or a salt thereof resulted in a significant mitigation of pain.

The present invention has been developed on the above-mentioned finding.

The principal object of the present invention is to provide an injectable solution containing TRH or its salt and a trihydric to hexahydric sugar alcohol which exhibits remarkably reduced pain when administered to a host, especially subcutaneously or intramuscularly. Another object is to provide a method for preparing the injectable solution. Other objects will be made clear from the description and claims hereinafter.

According to the present invention, TRH may be used as the free base or in the form of a physiologically acceptable salt such as an acid addition salt e.g. an organic acid salt, (acetate, tartrate, citrate, etc.) or a mineral acid salt (hydrochloride, nitrate, etc.). The injectable solution of the present invention contains TRH or its salt, practically in the range of about 0.01 to about 5 percent (hereinafter, all percents are on a weight-/volume basis) and, advantageously, in the range of about 0.02 to 2 percent, in terms of free TRH.

The trihydric to hexahydric sugar alcohol in the present invention includes straight-chain sugar alcohols and cyclic sugar alcohols. The straight-chain sugar alcohol may be shown by the general formula $HOCH_2(CHOH)_nCH_2OH$ wherein n is an integer from 1 to 4, and includes hexitols such as sorbitol, mannitol, allitol, talitol, glucitol, iditol and dulcitol; pentitols such as xylitol, adonitol (also called ribitol) and arabitol; tetritols such as erythritol and threitol; and triols such as glycerol. Among these straight-chain sugar alcohols hexitols and pentitols, especially hexitols, are advantageously employed. As the cyclic sugar alcohol there may be preferably employed inositol, which may be shown by the formula $C_6H_6(OH)_6$ and exemplified by meso-inositol. While some of these sugar alcohols exist in stereoisomers (geometric isomers or/and optical isomers), the present invention can be practiced with the employment of any of such forms of alcohols. These sugar alcohols may be employed alone or in combination.

To accomplish the object of making an injection painless, the sugar alcohol is desirably added at a level that will make the osmotic pressure of the injectable solution substantially isotonic, especially just isotonic or slightly hypertonic. Although the level of addition of the sugar alcohol varies with the concentration of TRH or its salt and the particular sugar alcohol used, it is generally advantageous that the alcohol be incorporated in the solution at a level of about 2 to about 9 percent and, for still better results, about 4 to about 8 percent.

The preparation of the injectable solution of the present invention can be accomplished by a procedure similar to that known in the art. For example, an injectable solution can be produced by dissolving TRH or a salt thereof and said sugar alcohol in distilled water for injection and adjusting the pH of the mixed solution. The pH of the solution is normally adjusted to the range of about 3 to about 7.5, preferably the range of about 3.5 to about 6.5, especially around 6. For this adjustment of pH there may be conveniently employed, for example, hydrochloric acid or sodium hydroxide which may be chosen depending upon the form of TRH employed, i.e. the free base or the physiologically acceptable salts.

Practically, it is advantageous to make the injectable solution substantially free from other electrolytes, as solutes, than TRH or its salt and the sugar alcohol. For example, the injectable solution desirably does not contain any substantial amount (e.g. not less than 0.1%) of sodium chloride, because it will interfere with the pain-reducing action of the sugar alcohol. Thus, it is most advantageous that the injectable solution consists essentially of TRH or its salt and the sugar alcohol as solutes and water as solvent, and that the pH thereof is adjusted to the range of about 3 to about 7.5. It is to be noted that the said pH adjustment can be achieved by the addition of a slight amount (e.g. less than 0.1%) of hydrochloric acid, sodium hydroxide or the like.

By virtue of the concomitant presence of the sugar alcohol, the injectable solution of this invention exhibits remarkably reduced pain and is stable as compared with the conventional TRH injections, with no particular side effects being noticed. Therefore, it is suitable, especially, for subcutaneous or intramuscular administration to a host (human beings; domesticated animals, e.g. dogs and cats; laboratory animals, e.g. rats and mice).

The injectable solution of the present invention may be employed in the same manner as the conventional TRH injectable solutions as, for example, diagnostic reagents for testing the thyrotropin-secreting function and drugs for the treatment of impaired consciousness.

The effect of the present invention will hereinafter be described by way of experimental data and working examples which, however, should not be construed as limiting the scope of the invention.

EXPERIMENT

Aqueous solutions were prepared by incorporating 0.5 mg. (in terms of free TRH) of TRH or TRH tartrate in 1 ml. portions of distilled water for injection and the solutions were each rendered isotonic by the addition of one of the sugar alcohols mentioned in Table 2 or sodium chloride as control and adjusted to the pH value mentioned in Table 2 with hydrochloric acid or sodium hydroxide. Each aqueous solution was filtered through a membrane filter and filled into a white ampoule of 1 ml. capacity, which was sealed and autoclaved. The injectable solutions thus obtained were subjected to a pain test using rabbits. The testing procedure comprised injecting 0.2 ml. of each test product subcutaneously into the dorsal ear of rabbits that were under unrestricted condition. The intensity of pain was scored on the scale of Table 1 based on the degree of escaping motion and the behavior of the rabbits at and after the injection.

Table 1

| Score | Observation at and after injection |
|---|---|
| − | No pain reaction |
| + | A slight escaping reaction at injection; the animals shake their head a few times after injection |
| ++ | A fairly prominent escaping reaction at injection; the animals shake their head violently after injection |
| +++ | A strong escaping reaction; the animals cry |

The results, as shown in Table 2, clearly indicate that while sodium chloride-isotonicated aqueous solutions of TRH or its salt produced intense pains, the sugar alcohol-isotonicated injectable solutions of this invention invariably did not elicit pain reactions.

Table 2

| Additive and its concentration (per ml.) | Form of TRH | pH | Degree of pain |
|---|---|---|---|
| Sodium chloride 9 mg. | Free | 3.5 | ++ |
| Sodium chloride 9 mg. | " | 4.5 | ++ |
| Sodium chloride 9 mg. | " | 5.5 | ++ |
| Sodium chloride 9 mg. | " | 6.5 | ++ |
| Sodium chloride 9 mg. | Tartrate | 3.5 | ++−+++ |
| Sodium chloride 9 mg. | " | 4.6 | ++ |
| Sodium chloride 9 mg. | " | 5.5 | ++ |
| Sodium chloride 9 mg. | " | 6.6 | ++ |
| D-mannitol 50 mg. | Free | 4.1 | − |
| D-mannitol 50 mg. | " | 6.0 | − |
| D-mannitol 50 mg. | Tartrate | 3.9 | − |
| D-mannitol 50 mg. | " | 6.0 | − |
| meso-Inositol 50 mg. | Free | 4.1 | − |
| meso-Inositol 50 mg. | " | 6.0 | − |
| meso-Inositol 50 mg. | Tartrate | 4.0 | − |
| meso-Inositol 50 mg. | " | 5.9 | − |
| D-sorbitol 50 mg. | Free | 4.1 | − |
| D-sorbitol 50 mg. | " | 6.1 | − |
| D-sorbitol 50 mg. | Tartrate | 4.1 | − |
| D-sorbitol 50 mg. | " | 5.9 | − |
| D-xylitol 50 mg. | Free | 4.0 | − |
| D-xylitol 50 mg. | " | 6.1 | − |
| D-xylitol 50 mg. | Tartrate | 3.9 | − |
| D-xylitol 50 mg. | " | 5.9 | − |
| Glycerol 19.4 mg. | Free | 3.9 | − |
| Glycerol 19.4 mg. | " | 6.0 | − |
| Glycerol 19.4 mg. | Tartrate | 4.1 | − |
| Glycerol 19.4 mg. | " | 6.0 | − |

EXAMPLE 1

An aqueous solution was prepared by incorporating 0.732 mg. of TRH tartrate and 50 mg. of meso-inositol in 1 ml. of distilled water for injection and adjusting the mixture to pH 4.0 with sodium hydroxide. The solution was filtered through a membrane filter and filled into a white ampoule of 1 ml. capacity, which was then sealed and autoclaved. By this procedure was obtained an injectable solution.

EXAMPLE 2

An aqueous solution was prepared by incorporating 0.732 mg. of TRH tartrate and 50 mg. of D-sorbitol in 1 ml. of distilled water for injection and adjusting the mixture to pH 6.0 with sodium hydroxide. The solution was processed as in Example 1 to obtain an injectable solution.

EXAMPLE 3

An aqueous solution was prepared by incorporating 1 mg. of TRH and 19.4 mg. of glycerol in 1 ml. of distilled water for injection. The solution was processed as in Example 1 to obtain an injectable solution.

EXAMPLE 4

The procedure of Example 1 was repeated except that 50 mg. of D-xylitol was used in lieu of meso-inositol to prepare an injectable solution.

EXAMPLE 5

The procedure of Example 2 was repeated except that 50 mg. of D-mannitol was used in lieu of D-sorbitol to prepare an injectable solution.

What is claimed is:

1. An injectable solution, which contains L-pyroglutamyl-L-histidyl-L-prolinamide or its physiologically acceptable salt in an amount within the range of about 0.01 to about 5 percent, on a weight/volume basis, in terms of free L-pyroglutamyl-L-histidyl-L-prolinamide, and a sugar alcohol selected from the group consisting of a hexitol, a pentitol and inositol in an amount within the range of about 2 to about 9 percent on a weight/volume basis, said solution being free from sodium chloride.

2. A solution as claimed in claim 1, which consists essentially of said amount of L-pyroglutamyl-L-histidyl-L-prolinamide or its physiologically acceptable salt, said amount of sugar alcohol, and water, said solution having a pH within the range of about 3 to about 7.5.

3. A solution as claimed in claim 1, wherein the sugar alcohol is a hexitol or a pentitol.

4. A solution as claimed in claim 3, wherein the sugar alcohol is a hexitol.

5. A solution as claimed in claim 4, wherein the hexitol is D-sorbitol.

6. A solution as claimed in claim 1, wherein the sugar alcohol is inositol.

7. A solution as claimed in claim 1, which is substantially isotonic.

8. A solution as claimed in claim 1, having a pH which is in the range of about 3 to about 7.5.

9. A solution as claimed in claim 1, wherein the physiologically acceptable salt is tartrate.

* * * * *